(12) United States Patent
Debras et al.

(10) Patent No.: US 6,420,303 B1
(45) Date of Patent: Jul. 16, 2002

(54) PRODUCTION OF POWDER CATALYSTS

(75) Inventors: Guy Debras, Frasnes-lez-Gosselies; Alain Standaert, Brussels; Hendrik D'Haese, Geraardsbergen, all of (BE)

(73) Assignee: Fina Research, S.A., Feluy (BE)

( * ) Notice: Subject to any disclaimer, the term of this patent is extended or adjusted under 35 U.S.C. 154(b) by 0 days.

(21) Appl. No.: 09/461,071

(22) Filed: Dec. 14, 1999

(30) Foreign Application Priority Data

Jan. 18, 1999 (EP) .............................. 99100836

(51) Int. Cl.[7] .................................. B01J 31/00
(52) U.S. Cl. ..................... 502/172; 502/169; 502/171; 502/226; 568/851
(58) Field of Search .................. 502/169, 171, 502/172, 226; 568/851

(56) References Cited

U.S. PATENT DOCUMENTS

| | | | |
|---|---|---|---|
| 4,194,992 A | * | 3/1980 | Corbellini et al. .......... 502/226 |
| 4,277,589 A | | 7/1981 | Giannini et al. ............ 526/122 |
| 4,636,486 A | | 1/1987 | Mayr et al. ................. 502/121 |
| 4,650,778 A | * | 3/1987 | Klabunde et al. ........... 502/226 |
| 5,212,132 A | * | 5/1993 | Spitz et al. ................. 502/226 |
| 5,212,133 A | * | 5/1993 | Duranel et al. ............. 502/226 |
| 5,492,984 A | * | 2/1996 | Brems et al. ............... 502/172 |
| 5,710,229 A | * | 1/1998 | Garoff et al. ............... 502/127 |

FOREIGN PATENT DOCUMENTS

| | | |
|---|---|---|
| EP | 0488856 | 6/1992 |
| EP | 0654485 | 5/1995 |
| EP | 0749983 | 12/1996 |

OTHER PUBLICATIONS

"Magnesium chloride—ethanol adducts", J.C.J. Bart and W. Roovers, Journal of Material Science, vol. 30, pp. 2809–2820 (1995).

* cited by examiner

Primary Examiner—Mark L. Bell
Assistant Examiner—J. Pasterczyk
(74) Attorney, Agent, or Firm—Gilbreth & Associates

(57) ABSTRACT

A process for the production of a magnesium chloride powder for use in a catalyst, the process comprising vaporizing magnesium chloride in a plasma torch and quenching the vapor with a liquid containing an electron donor to form a magnesium chloride-based powder catalyst wherein at least 80% by weight of the magnesium chloride is present as the hexagonal phase thereof. The invention also relates to a precursor for such a catalyst.

10 Claims, 3 Drawing Sheets

PRODUCTION OF POWDER CATALYSTS

The present invention relates to a process for the production of powder catalysts comprising titanated magnesium chloride and to a precursor for such a catalyst.

U.S. Pat. No. 4,650,778 discloses the production of metal halide particles useful as olefin polymerization catalyst precursors by vaporising the metal halide and then condensing it in the presence of a diluent.

It is also known for example from EP-A-0654444 and EP-A-0654485 to produce powder catalysts based on magnesium chloride, titanium chloride and at least an electron donor by using a plasma torch which vaporizes the compounds introduced into the plasma torch and the vapour is condensed to form a fine magnesium chloride powder covered with titanium chloride. The powder is employed as a catalyst in the polymerisation of alpha-olefins.

While those latter two prior specifications, both of which are in the name of the present applicant, disclose the production of catalysts having good activity in the polymerisation of alpha-olefins, nevertheless there is still the demand for such catalysts with yet higher activity.

U.S. Pat. No. 4,636,486 discloses a chemical preparation process for a magnesium halide supported Ziegler-Natta catalysts, the most active anhydrous magnesium chloride is obtained when its x-ray diffraction spectrum is characterised by a broadened halo appearing at a lattice distance (d) within the range of from 2.56 to 2.95 Angstroms. This may be compared to a very crystalline magnesium chloride which exhibits an intense diffraction line at a lattice distance (d) of 2.56 Angstroms. Thus this prior patent document discloses that a polymerisation catalyst based on anhydrous magnesium dichloride has improved activity.

The chemical process disclosed in this document is however a multi-step procedure which is more expensive than the plasma torch processes disclosed in the two European specifications mentioned above.

The present invention provides a process for the production of a magnesium chloride powder for use in a catalyst, the process comprising vaporising magnesium chloride in a plasma torch and quenching the vapor with a liquid containing an electron donor to form a magnesium chloride-based powder wherein at least 80% by weight of the magnesium chloride is present as the hexagonal phase thereof.

Preferably, the electron donor is dissolved in an organic diluent in an amount of at least 2 vol % based on the amount of diluent.

Preferably, the electron donor is present in an amount of from 2.5 to 10 vol % based on the amount of diluent.

Preferably, the electron donor is selected from tetrahydrofuran (THF), 1,3 dioxolane, dioxane, diethyl ether, methyl tert-butyl ether, diisobutyl phthalate, di-n-butyl phthalate, ethyl n-butyl phthalate, diethyl phthalate, ethyl i-butyl phthalate and mixtures thereof.

Preferably, the vapour is quenched at a temperature of below −10° C. to condense the magnesium chloride powder. The quenching step may be followed by a titanation step in which the magnesium chloride powder is titanated to form a catalyst for polymerising alpha-olefins.

Preferably, the titanated catalyst has a median particle size d50 of from 5 to 50 microns and more preferably from 8 to 35 microns.

Preferably, the titanated catalyst has an activity in the polymerisation of polyethylene of at least 20000 grams of polyethylene per gram of catalyst per hour.

The present invention provides a precursor for a magnesium chloride-based catalyst for polymerising alpha-olefins, the precursor comprising a magnesium chloride/tetrahydrofuran complex wherein at least 80% by weight of the magnesium chloride is present as the hexagonal phase thereof.

In contrast to the teaching of U.S. Pat. No. 4,636,486, the present inventor has discovered that in the manufacture of a magnesium chloride-based polymerisation catalyst the use of magnesium chloride powder having a significant proportion, typically at least 80% by weight, of the hexagonal crystalline form of the magnesium chloride, and thus having a very crystalline structure, can result in this very crystalline structure being transformed into a highly active catalyst by subsequent treatment by titanation, for example by titanium tetrachloride. If the crystalline structure of the magnesium chloride powder is less than 100% hexagonal, the remainder of the magnesium chloride is present in the rhombohedral crystalline phase. The present inventor has discovered that catalysts prepared using rhombohedric magnesium chloride have a relatively low activity in alpha-olefinic, e.g. ethylene, polymerisation as compared to catalysts prepared using hexagonal magnesium chloride. The hexagonal form of magnesium chloride tends to be less stable than the rhombohedric form. In accordance with the present invention, the magnesium chloride powder is formed by a plasma torch technique employing particular quenching conditions which increase the yield of the hexagonal phase of the magnesium chloride powder by forming a stable complex of the hexagonal magnesium-chloride with an electron donor, such as, for example, tetrahydrofuran (THF). This acts as a precursor for the subsequently titanated catalyst. In addition, the quenching conditions can be controlled to yield high catalyst activity in the resultant titanated catalyst, with a low median particular size of the catalyst powder.

The present invention will now be described by way of example only with reference to the accompanying drawings, in which.

Figure 1:
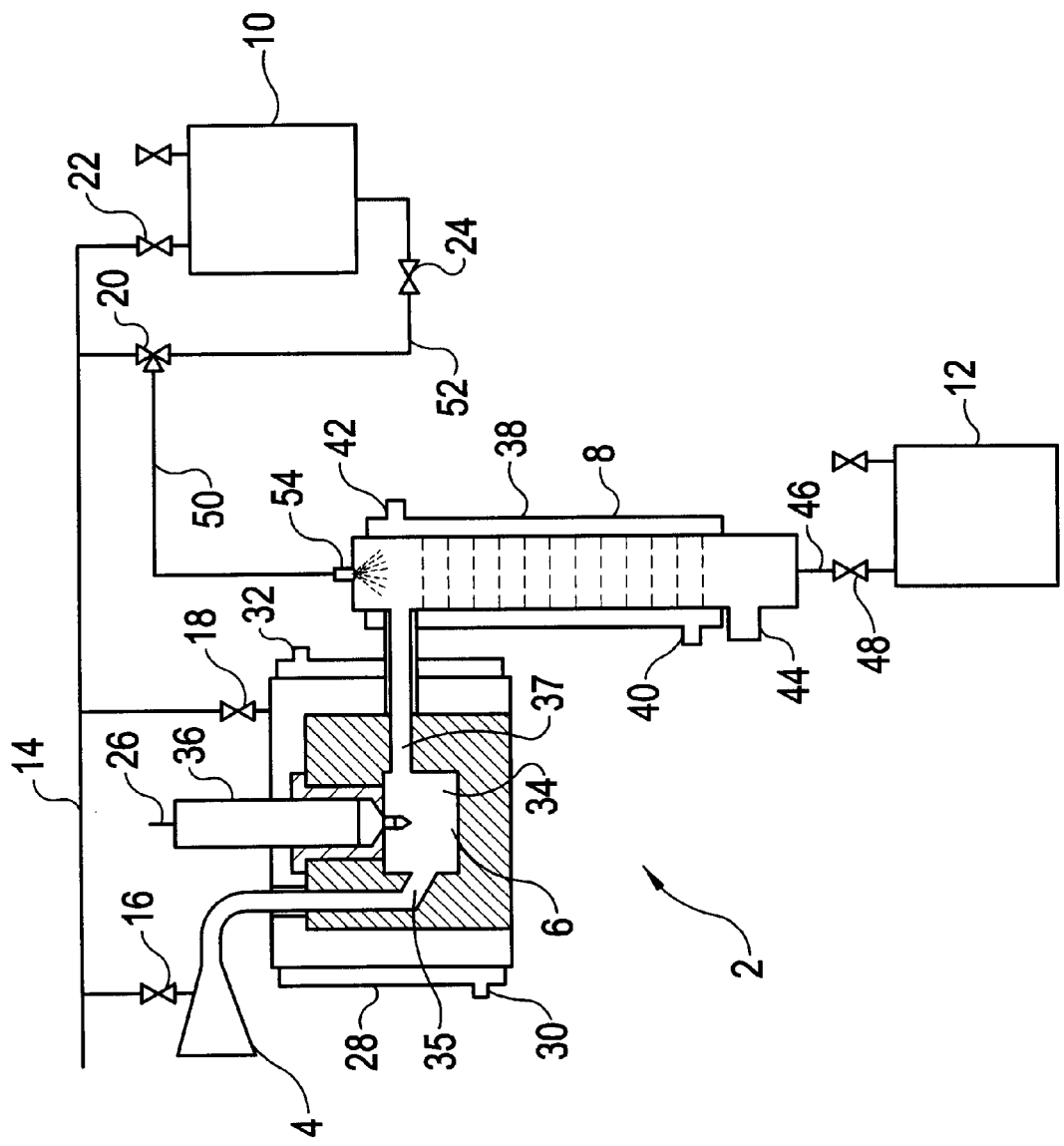
FIG. 1 is a schematic view of a plasma torch apparatus for use in an embodiment of the process of the invention.

Referring to FIG. 1, there is shown a plasma torch apparatus, designated generally as 2 for producing a magnesium chloride powder in accordance with an embodiment of the process of the present invention. The plasma torch apparatus 2 is composed of five different sections: a magnesium chloride injection unit 4, a furnace 6, a quenching column 8, a diluent unit 10, and a recovery unit 12.

The plasma torch apparatus 2 is connected to a source of nitrogen (not shown) and a nitrogen line 14 is connected to the magnesium chloride injection unit 4, the furnace 6, the quenching column 8 and the diluent unit 10 by respective valves 16, 18, 20 and 22. This enables the whole apparatus 2 or selected parts of the apparatus 2 to be purged under nitrogen and for the magnesium chloride to be introduced into the injection unit 4 under nitrogen. The furnace 6 is provided with a cooling jacket 28 having a cooling water inlet 30 and a cooling water outlet 32. The furnace 6 is provided with a central cavity 34 into which extends a plasma torch 36 connected to a source of helium (not shown) along a line 26. The cavity 34 is connected at its inlet end 35 to the magnesium chloride injection unit 4 and at its outlet end 37 to the quenching column 8.

The quenching column 8, downstream of the furnace 6, is vertically oriented and surrounded by a cooling jacket 38 having a cooling fluid inlet 40 and a cooling fluid outlet 42. At its bottom end the quenching column 8 is provided with a fume outlet 44 and a line 46 connected, via a valve 48, to the recovery unit 12 for recovering the quenched magnesium chloride powder. The upper end of the quenching column 8 is connected via a line 50 to the valve 20, thence via a line 52 via the valve 24 to the diluent unit 10. In use, diluent containing an electron donor is conveyed from the diluent unit 10 along lines 52 and 50 thereby to be injected into the top of the quenching column 8 via an injection nozzle 54.

In use, the apparatus 2 is purged under a nitrogen flow for a number of hours, typically overnight. Anhydrous magnesium chloride, typically 50 grams thereof, is introduced under nitrogen into the injection unit 4 and the diluent unit 10 is filled with diluent, for example hexane or toluene, containing an electron donor. The electron donor may be selected from tetrahydrofuran (THF), 1,3 dioxolane, dioxane, diethyl ether, methyl tert-butyl ether, diisobutyl phthalate, di-n-butyl phthalate, ethyl n-butyl phthalate, diethyl phthalate, ethyl i-butyl phthalate and mixtures thereof. The preferred electron donor is THF. The electron donor is preferably present in a concentration of at least 2 vol % based on the amount of diluent i.e. at least 20 ml electron donor per liter of diluent. Preferably, the amount of electron donor is from 2.5 to 10 vol % based on the volume of diluent. In order to dry the equipment, the plasma torch 36 is activated under a helium flow from line 26. Typically, the plasma torch 36 is operated under a current of 450 amps and a voltage of 40 volts under a helium flow of around 20 liters per minute.

Immediately after the drying step, the anhydrous magnesium chloride is introduced by the injection unit 4 into the cavity 34 of the furnace 6 at a flow of typically 2.5 grams per minute through a feed device, for example a motorised Archimedean screw. At the same time, the diluent having the electron donor dissolved therein and cooled to a temperature of typically −15° C. is injected into the quenching column 8 through the injection nozzle 54. The injection column 8 is cooled to a temperature below about −10° C. by a passage of the cooling fluid through the jacket 38.

In the furnace, under the current, voltage and helium flow conditions specified above, the plasma torch 36 is energized thereby to vaporize the magnesium chloride introduced into the cavity 34. Magnesium chloride vaporizes under standard pressure conditions at a temperature of about 1400° C. but a minimum temperature in the plasma zone of the furnace 6 i.e. in the cavity 34, of around 2000° C. would be generated by the plasma torch 36 in order rapidly to vaporize the magnesium chloride in accordance with the invention. The vaporized magnesium chloride is conducted to the quenching column 8 under the helium flow where it is quickly precipitated as an "activated" solid due to the very low temperatures in the quenching column 8. The diluent which is injected into the quenching column 8 by the injection nozzle 54 condenses the magnesium chloride vapor and forms a complex between the electron donor, preferably THF, in the diluent and the condensed magnesium chloride. The diluent is only introduced into the quenching column 8 downstream of the furnace and is not vaporized with the magnesium chloride. The bottom of the quenching column 8 is connected via the line 46 and the valve 48 to the recovery unit 12 in which a slurry of the condensed magnesium chloride powder in the diluent is collected under a nitrogen blanket. After the termination of the introduction of the magnesium chloride into the furnace 6, the vaporization and the quenching of the vapor by the diluent in the quenching column 8 are continued in order to complete precipitation and recovery of the magnesium chloride.

In a modification of the process conditions described above, the plasma torch 36 may be operated under transfer conditions, wherein in addition to the plasma torch 36 being powered as described above, the bottom of the furnace 6 is subjected to a current of 150 amps and a voltage of 30 volts. This can improve the conversion yield of the magnesium chloride and the yield of the "activated species" of the magnesium chloride.

Finally, the magnesium chloride slurry is decanted from the recovery unit 12 and transferred to a bottle in which the product is washed a number of times, for example four times, with an organic liquid such as heptane or alternatively once with a 1 wt % solution of triethyl aluminum (TEAL) in heptane and then with pure heptane until no TEAL is detected in the washing diluents by reaction with titanium tetrachloride. The heptane washes may be carried out at a temperature of typically 60° C. The resultant magnesium chloride solid powder is stored as a suspension in heptane.

The magnesium chloride powder so obtained may then be subjected to a titanation step in order to prepare the resultant polyolefin polymerisation catalyst. Typically the titanation step may be carried out by adding titanium tetrachloride to the magnesium chloride suspension in heptane under nitrogen and under agitation. Typically, 20 ml of the magnesium chloride suspension and 100 ml of heptane are introduced under nitrogen into a flask and then 20 ml of titanium tetrachloride are added to the suspension under agitation. The suspension is then refluxed over night and after cooling down to a temperature of around 70° C., the solid is decanted off and the liquid eliminated. The solid is then resuspended in heptane and washed four times by decantation. Finally, the solid catalyst is suspended in heptane and stored in the dark.

In a subsequent polymerisation process, typically the catalyst so obtained is activated with a co-catalyst, which may be selected from an aluminum alkyl such as TEAL or trisobutyl aluminum (TIBAL) and introduced into a polymerisation reactor at a given temperature containing isobutane (as an inert diluent), ethylene and hydrogen. The polymerisation conditions are maintained for typically one hour and the reactor is then flushed and the polymer recovered. The amount of solid polymerisation product is then determined and the activity of the catalyst is calculated based on the polymer weight and the magnesium content.

Using the above-described plasma torch apparatus and process, the inventor discovered surprisingly that by injecting THF into the quenching column 8 in an amount of at least 20 ml THF per liter of diluent, and preferably with the temperature in the quenching column being cooled to below −10° C., the resultant magnesium chloride, as observed by x-ray diffraction, contained at least 80% by weight, more preferably at least 85% by weight of the hexagonal phase, as compared to the rhombohedral phase which is either absent or present in a minor amount of up to 20 wt % or up to 15 wt %.

Figure 2:
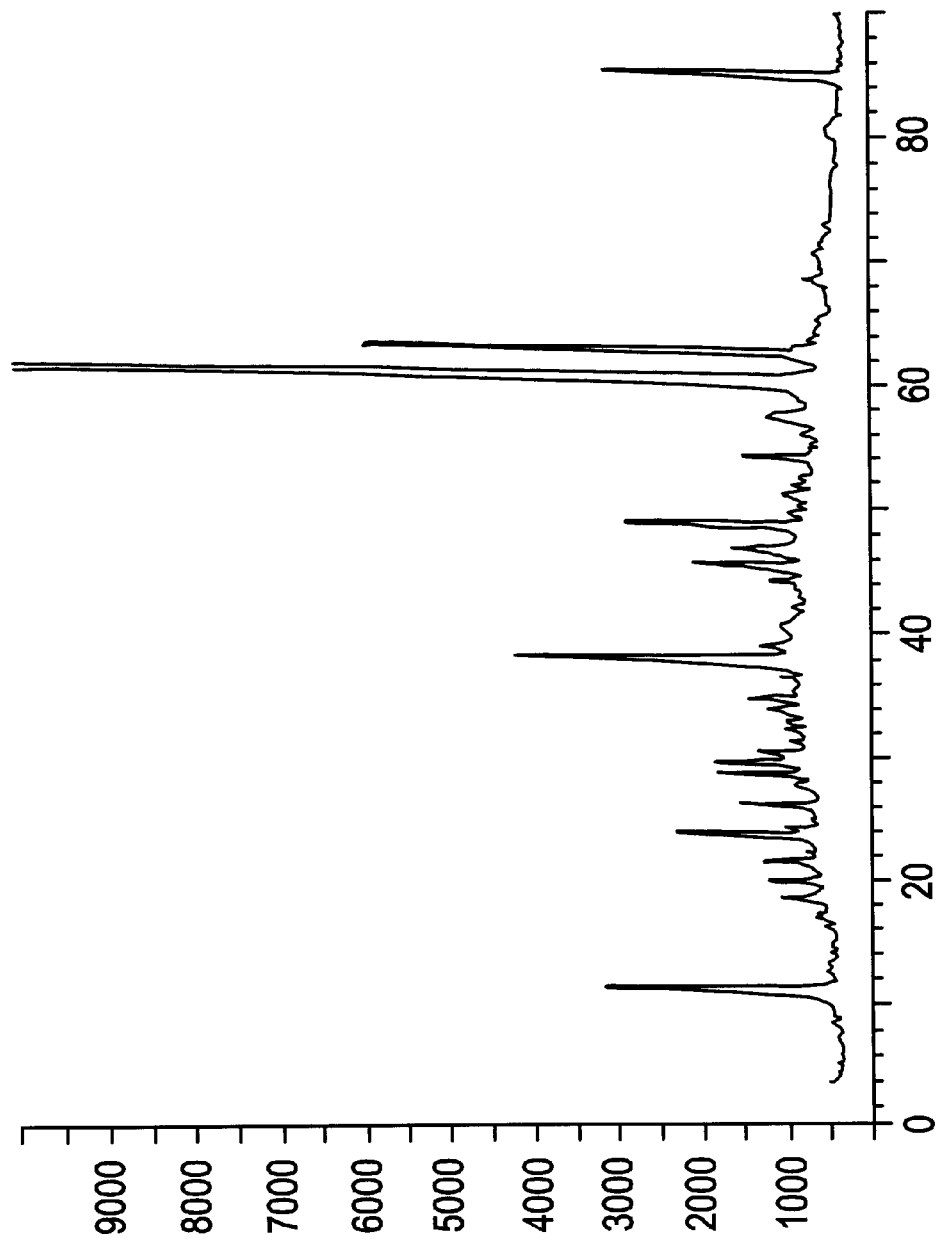
FIG. 2 is a graph showing an x-ray diffraction spectrum of a magnesium chloride powder/tetrahydrofuran complex produced in accordance with an embodiment of the process of the invention.

FIG. 2 is an x-ray diffraction pattern of a magnesium chloride/THF complex formed in accordance with the present invention prior to titanation. Peak 1 at a value of the angle $2\Theta$ of around 40 represents the amount of the rhombohedral magnesium chloride and peak 2 at a value of the angle $2\Theta$ of around 38 represents the amount of the hexagonal magnesium chloride. It will be seen that the magnesium chloride/THF complex has a very high hexagonal/rhombohedric ratio, preferably more than 3.5:1, more preferably greater than 5:1 and typically around 5.8:1 as measured by x-ray diffraction, the amount of each phase being represented by the area under the respective peak for each peak in the x-ray diffraction pattern.

The hexagonal phase of the magnesium chloride tends to be less stable than the rhombohedral phase. However, it is believed, without being bound by theory, that the use of THF in the quenching stage tends to act as a template for the hexagonal phase and thereby stabilises the relatively unstable hexagonal phase at the low quenching temperature by forming a hexagonal magnesium chloride/THF complex. The hexagonal magnesium chloride/THF complex is destroyed during the subsequent titanation step.

Figure 3:
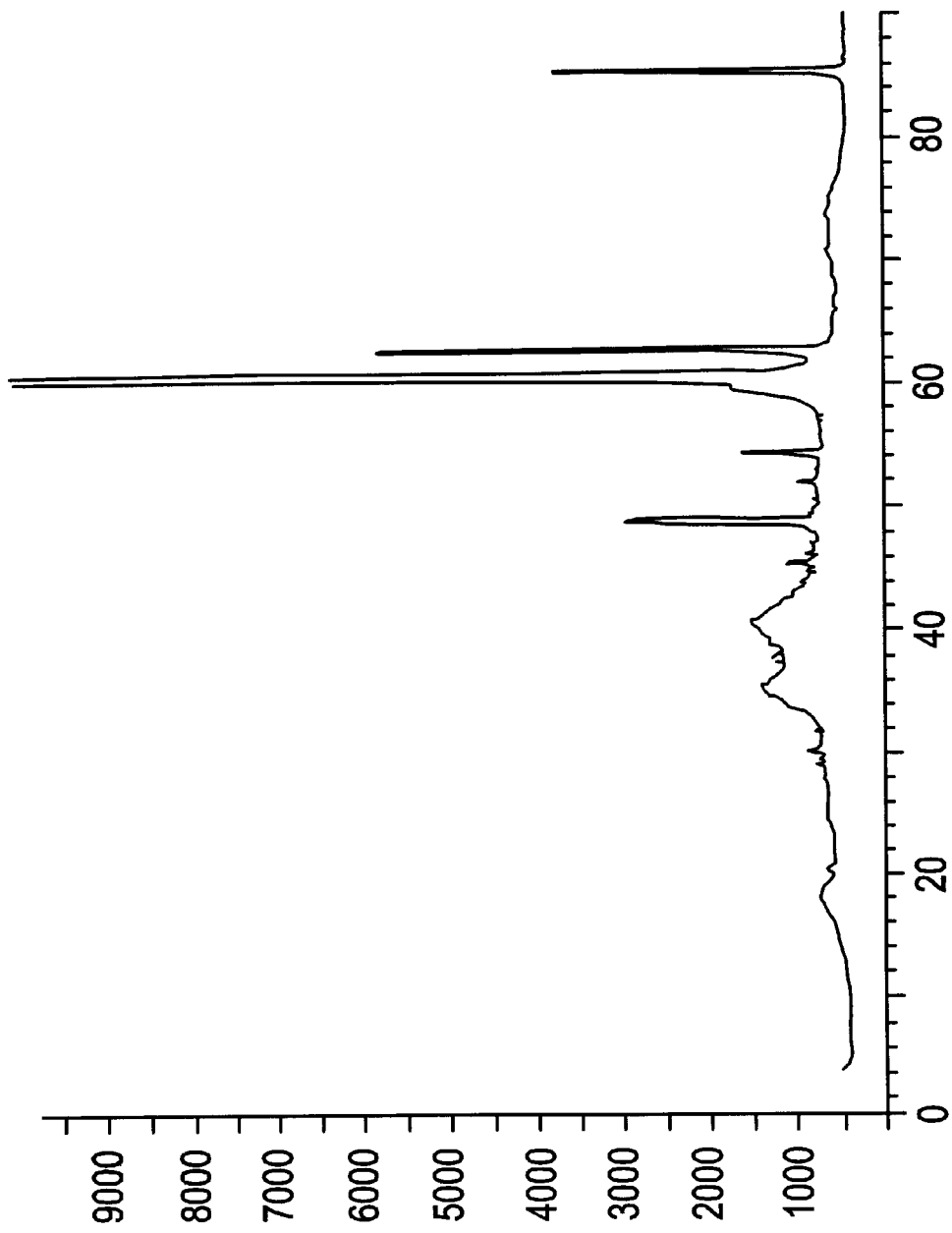
FIG. 3 is a graph showing an x-ray diffraction spectrum of a titanated magnesium chloride-based catalyst produced in accordance with an embodiment of the present invention.

After the titanation step, the resultant titanated magnesium chloride is substantially disordered and exhibits good catalyst activity and low median particle sizes (d50). The x-ray diffraction pattern of a catalyst of the invention formed by titanation of a hexagonal magnesium chloride/THF complex is illustrated in FIG. 3. This shows a "halo" in the diffraction pattern (i.e. a lack of distinct diffraction peaks) around values of the angle $2\Theta$ of from 34 to 42 indicating the presence of a disordered compound of the titanated magnesium chloride.

The present invention will now be described in greater detail with reference to the following non-limiting Examples.

EXAMPLE 1

In this Example, a magnesium chloride/THF complex was formed using the process conditions described above with respect to the apparatus of FIG. 1, the furnace being operated under transfer conditions. The THF was dissolved in toluene as a diluent in an amount of 25 ml/l (2.5 vol % THF based on the volume of the diluent). The THF/toluene liquid was injected through the injector 54 into the quenching column 8 held at a temperature of below −10° C. in order to condense out the magnesium chloride vapour. The resultant magnesium chloride powder complex with THF was analysed by x-ray diffraction which showed that the magnesium chloride had a hexagonal crystalline structure. Following titanation with titanium tetrachloride as described hereinabove, the resultant catalyst had a median particle size d50 of 8 microns and an activity in the production of polyethylene of 36000 gPE/gcat.hour.

Thus the use of THF dissolved in the toluene in the quenching step yielded a hexagonal magnesium chloride which, following titanation to produce a catalyst, resulted in the catalyst having small particle size and high activity.

EXAMPLE 2

Example 2 was carried out in the manner described above with respect to Example 1 but the THF was dissolved in hexane in an amount of 25 ml/l of diluent and the x-ray diffraction pattern again indicated that the resultant magnesium chloride had a hexagonal crystalline structure. Following titanation by titanium tetrachloride, the resultant catalyst had a median particle size d50 of 30 microns and an activity of 20000 gPE/gcat.hour.

EXAMPLE 3

Example 2 was repeated to produce the same hexagonal magnesium chloride. The resultant $MgCl_2$.THF complex was washed three times with 1 wt % TEAL hexane solution. After a final heptane washing, the product was titanated by titanium tetrachloride. This yielded a catalyst having a median particle diameter d50 of 34 microns and an activity of 31000 gPE/gcat.hour.

EXAMPLE 4

Example 2 was repeated but with the furnace being powered at 40 V, 530 A and not being under transfer conditions. The amount of THF was 25 ml/l in a solvent of toluene. A magnesium chloride/THF complex having a major portion of hexagonal phase $MgCl_2$ and a minor portion of rhombohedral phase $MgCl_2$ was produced. FIG. 2 is the x-ray diffraction pattern of the resultant $MgCl_2$ which has a hexagonal/rhombohedral ratio as measured by x-ray diffraction of 5.8:1. FIG. 3 is the diffraction pattern of the $MgCl_2$ of FIG. 2 following titanation as discussed hereinabove.

Comparative Example 1

Example 2 was repeated but the amount of THF in the hexane was only 2 ml/l. This yielded a magnesium chloride having a hexagonal/rhombohedral ratio, as observed by x-ray diffraction, of 3.5. Following titanation by titanium tetrachloride, the resultant catalyst had a median particle size d50 of 9 microns but an activity of only 10000 gPE/gcat.hour. This indicates that the use of greater amounts of THF in accordance with Example 1 results in a catalyst having greater activity.

Comparative Example 2

Comparative Example 1 was repeated by omitting any THF in the quenching column and using pure hexane. The resultant magnesium chloride had a hexagonal/rhombohedric ratio of only 0.4. Following titanation by titanium tetrachloride, the resultant catalyst had a median particle size d50 of 15 microns and an activity of only 2000 gPE/gcat.hour.

In contrast to the catalysts produced in accordance with the invention, typical commercial catalysts based on magnesium chloride have for example a median particle size d50 of 10 microns and an activity of 32000 gPE/gcat.hour or a median particle size d50 of 35 microns and an activity of 23000 gPE/gcat.hour. It is believed that these lower activities in ethylene polymerisation result from the existence of the catalyst being prepared using the relatively more thermally stable rhombohedric magnesium chloride. In accordance with the present invention, the use of THF in the quenching column as an electron donor tends to yield the hexagonal phase of the magnesium chloride being predominantly or exclusively present and the THF forms a complex with the magnesium chloride which tends to stabilise the thermodynamically unstable hexagonal phase to prevent it reverting to the rhombohedral phase. The corresponding resultant catalysts have a high activity, at least comparable or even higher than the activity of commercial catalysts based on magnesium chloride.

What is claimed is:

1. A process for the production of a magnesium chloride powder for use in a catalyst, the process consisting essentially of:
   (a) vaporizing magnesium chloride in a plasma torch; and
   (b) quenching the vapor with a liquid containing an electron donor to form a magnesium chloride-containing powder, in which at least 80% by weight of the magnesium chloride is present as the hexagonal phase thereof.

2. A process according to claim 1 wherein the quenching step is followed by:
   c) titanating the magnesium chloride powder to form a titanated catalyst for polymerisation alpha-olefins.

3. A process according to claim 2 wherein the titanated catalyst has a median particle size of from 8 to 34 microns.

4. A process according to claim 1 wherein the plasma torch vaporises the magnesium chloride at a temperature of at least 2000° C.

5. A process according to claim 1 wherein at least 85% by weight of the magnesium chloride is present as the hexagonal phase thereof.

6. A process according to claim 1 wherein the magnesium chloride is vaporized in a furnace, which has a bottom part thereof, provided with electrical power thereby to enhance the vaporization of the magnesium chloride.

7. A process according to claim 1 wherein the vapour is quenched at a temperature of below −10° C. to condense the magnesium chloride powder.

8. A process according to claim 1, wherein the electron donor is selected from the group consisting of tetrahydrofuran (THF), 1,3-dioxolane, dioxane, diethyl ether, methyl tert-butyl ether, diisobutyl phthalate, di-n-butyl phthalate, ethyl n-butyl phthalate, diethyl phthalate, ethyl i-butyl phthalate and mixtures thereof.

9. A process according to claim 1 wherein the electron donor is dissolved in an organic diluent in an amount of at least 2 vol % based on the amount of diluent.

10. A process according to claim 9 wherein the electron donor is present in an amount of from 2.5 to 10 vol % based on the amount of diluent.

* * * * *